United States Patent
Harada et al.

(10) Patent No.: US 9,125,609 B2
(45) Date of Patent: Sep. 8, 2015

(54) PORTABLE TERMINAL HAVING FUNCTION OF MEASURING MENTAL FATIGUE, METHOD FOR MEASURING SAME AND SERVER COMPUTER

(75) Inventors: Nobuyoshi Harada, Ikeda (JP); Sunao Iwaki, Ikeda (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 965 days.

(21) Appl. No.: 13/063,289

(22) PCT Filed: Aug. 27, 2009

(86) PCT No.: PCT/JP2009/064981
§ 371 (c)(1),
(2), (4) Date: Apr. 28, 2011

(87) PCT Pub. No.: WO2010/029857
PCT Pub. Date: Mar. 18, 2010

(65) Prior Publication Data
US 2011/0213269 A1    Sep. 1, 2011

(30) Foreign Application Priority Data
Sep. 11, 2008 (JP) ................................ 2008-232781

(51) Int. Cl.
A61B 13/00 (2006.01)
A61B 5/16 (2006.01)
A61B 5/00 (2006.01)

(52) U.S. Cl.
CPC ............... *A61B 5/161* (2013.01); *A61B 5/6887* (2013.01); *A61B 2560/0242* (2013.01)

(58) Field of Classification Search
CPC ........... A61B 5/16; A61B 3/113; A61B 5/162
USPC ....................................................... 600/558
See application file for complete search history.

(56) References Cited

U.S. PATENT DOCUMENTS 6,129,436 A    10/2000  Treskov et al.
6,540,663 B1    4/2003  Vau et al.
(Continued)

FOREIGN PATENT DOCUMENTS

JP    2001-189924 A    7/2001
JP    2001-309887 A    11/2001
(Continued)

OTHER PUBLICATIONS

Hecht S. et al., "Intermittent Stimulation by Light III. The Relation Between Intensity and Critical Fusion Frequency for Different Retinal Locations", The Journal of General Psychology, Accepted for Publication on May 24, 1933, pp. 251-268, cited in Supplementary European Search Report dated Mar. 31, 2014, issued in European Patent Application No. 09813004.0, w/English abstract.
(Continued)

*Primary Examiner* — Sean Dougherty
*Assistant Examiner* — Daniel Cerioni
(74) *Attorney, Agent, or Firm* — Westerman, Hattori, Daniels & Adrian, LLP

(57) ABSTRACT

A portable terminal device capable of measuring and evaluating mental fatigue, its measuring method, and a server computer is provided. The portable terminal device includes an operation unit; an imaging unit; a display screen or light emitting element; and a recording unit. Environmental data, which represents ambient environmental light, is calculated by capturing at least a reference image, first frequency data measured when the user is healthy is associated with first environmental data at the time of the measurement, and the associated data is stored in the recording unit; and a proportion of decrease of second frequency data measured when the user is not healthy from the first frequency data associated with the first environmental data having the same order of magnitude as that of second environmental data at the time of the measurement is calculated to evaluate the degree of fatigue of the user.

13 Claims, 6 Drawing Sheets

(56) References Cited

U.S. PATENT DOCUMENTS

| | | | | |
|---|---|---|---|---|
| 2009/0018419 A1* | 1/2009 | Torch | | 600/318 |
| 2010/0041002 A1* | 2/2010 | Harada et al. | | 434/236 |

FOREIGN PATENT DOCUMENTS

| | | | |
|---|---|---|---|
| JP | 2003-070773 | A | 3/2003 |
| JP | 2004-174041 | A | 6/2004 |
| JP | 2005-168856 | A | 6/2005 |
| JP | 2008-183048 | A | 8/2008 |
| WO | 2008097859 | A2 | 8/2008 |
| WO | 2008111425 | A1 | 9/2008 |

OTHER PUBLICATIONS

Supplementary European Search Report dated Mar. 31, 2014, issued in European Patent Application No. 09813004.0.

International Search Report of PCT/JP2009/064981, date of mailing Oct. 6, 2009.

Kazuo Saito; "Atarashii Hiro Hanteiho to shite No. VRT Oyobi Pocket Flicker ni Tsuite (VRT and Pocket CFF as the New Apparatus for Fatigue Measurement)", The Japanese journal of ergonomics, Apr. 10, 1989, vol. 25, Special Edition, pp. 144-145. Cited in ISR.

* cited by examiner (a)  (b)

n Lux

PORTABLE TERMINAL HAVING FUNCTION OF MEASURING MENTAL FATIGUE, METHOD FOR MEASURING SAME AND SERVER COMPUTER

TECHNICAL FIELD

The present invention relates to the measurement of human mental fatigue, particularly to a portable terminal device that has a function of measuring mental fatigue, its measuring method, and a server computer that manages information measured by the portable terminal device.

BACKGROUND ART

In recent years, health hazards and industrial accidents caused by mental fatigue due to overwork have become a social problem.

A flicker test is a known method of measuring mental fatigue. The test relies on human inability to perceive a light pulse, i.e., a flicker, when the light source is blinking at high speeds; however, as the speed (frequency) decreases, perception becomes possible when the frequency is dropped to a certain value. The frequency at which the human perceives the flicker is called a flicker perception threshold, which is known to vary depending on mental fatigue. More specifically, the flicker perception threshold decreases as fatigue becomes more intense; that is, a person cannot perceive a flicker at high frequency when mental fatigue is intense, and perception finally becomes possible when the frequency is dropped to a smaller value than that of a frequency of a flicker that is perceivable by a person in a healthy condition. Using this phenomenon, various flicker test methods and systems were suggested.

For example, Patent Literature 1 discloses a massage device that uses a portable terminal such as a PDA to measure a flicker value before and after a massage, and determines whether the degree of fatigue is improved by the massage.

Patent Literature 2 discloses a system in which a host computer remotely controls a computer terminal in front of the test subject via a network, so as to present some kind of stimulation to the test subject, control the stimulation, and record the reaction of the test subject, thereby measuring the functioning eyesight (actual eyesight) of eyes of the test subject under stress. The document also discloses a method of measurement of flicker perception eyesight to determine the ability to perceive a flicker, as an example of eyesight measurement.

Patent Literature 3 discloses a system comprising a blinking light emitting display device and a computer terminal. The blinking light emitting display device presents flicker stimulation under the control of a computer terminal via a communication cable, and the computer terminal records push-button operations involved in a flicker perception. The measurement data is compared with other data previously stored so as to measure the degree of fatigue.

Although Patent Literature 4 is not intended to measure a flicker value, it discloses a stress control system in which biological data is obtained from a sensor that is attached to a cell phone so as to be in contact with a user; based on the obtained data, the stress state is recognized with reference to psychophysiological parameters. Then, an inference engine is allowed to select an image, which can improve the stress state, and the selected image is displayed on the display screen of the cell phone.

CITATION LIST

Patent Literature

PTL 1: Japanese Unexamined Patent Publication No. 2004-174041
PTL 2: Japanese Unexamined Patent Publication No. 2001-309887
PTL 3: Japanese Unexamined Patent Publication No. 2003-70773
PTL 4: Japanese Unexamined Patent Publication No. 2001-189924

SUMMARY OF INVENTION

Technical Problem

None of Patent Literatures 1 to 3 carries out evaluation in consideration of the fact that the flicker perception frequency is influenced by ambient light. Therefore, the evaluation of mental fatigue is not accurate. The influence of ambient light may be eliminated by commanding the test subject to look into the measurement device or to press his/her eyes onto the measurement devices of Patent Documents 1 to 3. However, this forces the user into an uncomfortable posture, increasing the burden of the user.

Furthermore, in all of Patent Literatures 1 to 3, a computer and/or other dedicated device is used. Therefore, the user is not allowed to easily measure mental fatigue in an unspecified location. In addition, Patent Literature 4 does not relate to the measurement of a flicker value.

The present invention was made to solve the foregoing problems and aims to provide a portable terminal device that has a function of measuring mental fatigue, its measuring method, and a server computer. The portable terminal device of the present invention allows the user to easily and accurately measure and evaluate mental fatigue in any location without much difficulty.

Solution to Problem

The inventors of the present invention found that, because the flicker perception threshold of an individual having a generally healthy condition is stable, the mental fatigue of an individual after a given period of mental work can be quantified by measuring the change in the flicker perception threshold at the target time using the flicker perception threshold in a generally healthy condition as a standard value. The inventors further found that a more accurate evaluation of the degree of fatigue can be achieved if ambient light is taken into consideration. Based on these findings, the inventors completed the present invention wherein mental fatigue is measured by using a portable terminal device.

Specifically, a first portable terminal device according to the present invention capable of measuring mental fatigue comprises:

an operation unit;
an imaging unit for measuring ambient light;
a display screen for displaying a blinking image while a flicker frequency of the blinking image is being monotonically changed with time from a start frequency to an ending frequency; and
a recording unit for recording the flicker frequency, as a measurement frequency, at the time when a user operates the operation unit to indicate that the user perceives flicker during the display of the blinking image, wherein:

first frequency data, which is the measurement frequency measured when the user is specified as being healthy via the operation unit, is associated with first environmental data, which represents the ambient light measured by the imaging unit, and the associated data is stored in the recording unit; and a proportion of decrease of second frequency data, which is the measurement frequency measured when the user is not specified as being healthy via the operation unit, from the first frequency data associated with the first environmental data having the same order of magnitude as that of second environmental data, which represents the ambient light measured by the imaging unit, is calculated to evaluate a degree of fatigue of the user, and the degree of fatigue is displayed on the display screen, and wherein:

each of the first and second environmental data is a value calculated by $$K \times S_n / S_S,$$

using image luminance data $S_S$ obtained by capturing a reference image at a position having an illuminance of K; and image luminance data $S_n$ obtained by the imaging unit capturing the reference image at a position having an arbitrary illuminance.

A second portable terminal device according to the present invention capable of measuring mental fatigue comprises:

an operation unit;
an imaging unit for measuring ambient light;
a display screen;
a light-emitting element for displaying a blinking image while a flicker frequency of the blinking image is being monotonically changed with time from a start frequency to an ending frequency; and
a recording unit for recording the flicker frequency, as a measurement frequency, at the time when a user operates the operation unit to indicate that the user perceives flicker during the display of the blinking image, wherein:

first frequency data, which is the measurement frequency measured when the user is specified as being healthy via the operation unit, is associated with first environmental data, which represents the ambient light measured by the imaging unit, and the associated data is stored in the recording unit; and a proportion of decrease of second frequency data, which is the measurement frequency measured when the user is not specified as being healthy via the operation unit, from the first frequency data associated with the first environmental data having the same order of magnitude as that of second environmental data, which represents the ambient light measured by the imaging unit, is calculated to evaluate a degree of fatigue of the user, and the degree of fatigue is displayed on the display screen, and wherein:

each of the first and second environmental data is a value calculated by $$K \times S_n / S_S,$$

using image luminance data $S_S$ obtained by capturing a reference image at a position having an illuminance of K; and image luminance data $S_n$ obtained by the imaging unit capturing the reference image at a position having an arbitrary illuminance.

A third portable terminal device according to the present invention capable of measuring mental fatigue comprises:

an operation unit;
an imaging unit for measuring ambient light;
a display screen for displaying a blinking image while a flicker frequency of the blinking image is being monotonically changed with time from a start frequency to an ending frequency; and
a recording unit for recording the flicker frequency, as a measurement frequency, at the time when a user operates the operation unit to indicate that the user perceives flicker during the display of the blinking image, wherein:

first frequency data, which is the measurement frequency measured when the user is specified as being healthy via the operation unit, is associated with first environmental data, which represents the ambient light measured by the imaging unit, and the associated data is stored in the recording unit; and a proportion of decrease of second frequency data, which is the measurement frequency measured when the user is not specified as being healthy via the operation unit, from the first frequency data associated with the first environmental data having the same order of magnitude as that of second environmental data, which represents the ambient light measured by the imaging unit, is calculated to evaluate a degree of fatigue of the user, and the degree of fatigue is displayed on the display screen, and wherein:

each of the first and second environmental data is a value calculated by $$\alpha \times K \times H_p / S_S,$$

using image luminance data $S_S$ obtained by capturing a reference image at a position having an illuminance of K, image luminance data $H_p$ obtained by the imaging unit capturing a part of the user's body or an object that the user carries, and a correction factor $\alpha$.

A fourth portable terminal device according to the present invention capable of measuring mental fatigue comprises:

an operation unit;
an imaging unit for measuring ambient light;
a display screen;
a light-emitting element for displaying a blinking image while a flicker frequency of the blinking image is being monotonically changed with time from a start frequency to an ending frequency; and
a recording unit for recording the flicker frequency, as a measurement frequency, at the time when a user operates the operation unit to indicate that the user perceives flicker during the display of the blinking image, wherein:

first frequency data, which is the measurement frequency measured when the user is specified as being healthy via the operation unit, is associated with first environmental data, which represents the ambient light measured by the imaging unit, and the associated data is stored in the recording unit; and a proportion of decrease of second frequency data, which is the measurement frequency measured when the user is not specified as being healthy via the operation unit, from the first frequency data associated with the first environmental data having the same order of magnitude as that of second environmental data, which represents the ambient light measured by the imaging unit, is calculated to evaluate a degree of fatigue of the user, and the degree of fatigue is displayed on the display screen, and wherein:
each of the first and second environmental data is a value calculated by $$\alpha \times K \times H_p / S_S,$$

using image luminance data $S_S$ obtained by capturing a reference image at a position having an illuminance of K, image luminance data $H_p$ obtained by the imaging unit capturing a part of the user's body or an object that the user carries, and a correction factor $\alpha$.

A fifth portable terminal device according to the present invention capable of measuring mental fatigue is based on the above-described third or fourth portable terminal device,
wherein:
the part of the user's body captured is a palm of a hand, and the correction factor $\alpha$ is a value calculated by $$S_n/H_n,$$

using the image luminance data $S_n$ obtained by capturing the reference image, and image luminance data $H_n$ obtained by capturing the palm of a hand in the same light environment as the data $S_n$.

A first server computer according to the present invention determines an abnormal state of the user in accordance with a change in data measured by any of the first to fourth portable terminal devices,
wherein:
the first frequency data and first environmental data measured by the portable terminal device, and information of a time at which these data are measured are received from the portable terminal device and stored; and
when the second frequency data and second environmental data are received from the portable terminal device, and when the difference between the second frequency data and the first frequency data associated with the first environmental data having the same order of magnitude as that of the second environmental data is equal to or greater than a predetermined value, an abnormal state of the user is determined, and information corresponding to the determination result is transmitted to the portable terminal device.

A second server computer according to the present invention determines an abnormal state of the user in accordance with a change in data measured by any of the first to fourth portable terminal devices,
wherein:
the second frequency data and second environmental data measured by the portable terminal device, and information of a time at which these data are measured are received from the portable terminal device and stored; and
when new second frequency data and new second environmental data are received from the portable terminal device, the second frequency data associated with the second environmental data having the same order of magnitude as that of the new second environmental data is selected, and when a variation with time between the selected second frequency data and the new second environmental data differs from that of a weekend effect, an abnormal state of the user is determined, and information corresponding to the determination result is transmitted to the portable terminal device.

A third server computer according to the present invention determines an abnormal state of the user in accordance with a change in data measured by any of the first to fourth portable terminal devices,
wherein:
the second frequency data and second environmental data measured by the portable terminal device, and information of a time at which these data are measured are received from the portable terminal device and stored; and
acceleration data detected by an acceleration sensor that the user carries, and information of a time at which the acceleration data is detected are received and stored; and
a change in the second frequency data associated with the second environmental data having the same order of magnitude, and a change in the acceleration data, both of which occurred within a predetermined period, are evaluated to determine an abnormal state of the user, and information corresponding to the determination result is transmitted to the portable terminal device.

A first method for measuring mental fatigue according to the present invention is performed by using a portable terminal device comprising an operation unit, an imaging unit, a display screen, and a recording unit,
the method comprising the steps of:
1) measuring ambient light using the imaging unit;
2) displaying a blinking image on the display screen while a flicker frequency of the blinking image is being monotonically changed with time from a start frequency to an ending frequency;
3) recording the flicker frequency in the recording unit, as a measurement frequency, at the time when a user operates the operation unit to indicate that the user perceives flicker during the display of the blinking image;
4) associating first frequency data, which is the measurement frequency measured when the user is specified as being healthy via the operation unit, with first environmental data, which represents the ambient light measured by the imaging unit, and storing the associated data in the recording unit; and
5) calculating a proportion of decrease of second frequency data, which is the measurement frequency measured when the user is not specified as being healthy via the operation unit, from the first frequency data associated with the first environmental data having the same order of magnitude as that of second environmental data, which represents the ambient light measured by the imaging unit, to evaluate a degree of fatigue of the user, and displaying the degree of fatigue on the display screen,
wherein:
each of the first and second environmental data is a value calculated by $$K \times S_n/S_S,$$

using image luminance data $S_S$ obtained by capturing a reference image at a position having an illuminance of K, and image luminance data $S_n$ obtained by the imaging unit capturing the reference image at a position having an arbitrary illuminance.

A second method for measuring mental fatigue according to the present invention is performed by using a portable terminal device comprising an operation unit, an imaging unit, a display screen, a light-emitting element, and a recording unit,
the method comprising the steps of:
1) measuring ambient light using the imaging unit;
2) displaying a blinking image on the light-emitting element while a flicker frequency of the blinking image is being monotonically changed with time from a start frequency to an ending frequency;
3) recording the flicker frequency in the recording unit, as a measurement frequency, at the time when a user operates the operation unit to indicate that the user perceives flicker during the display of the blinking image;

4) associating first frequency data, which is the measurement frequency measured when the user is specified as being healthy via the operation unit, with first environmental data, which represents the ambient light measured by the imaging unit, and storing the associated data in the recording unit; and 5) calculating a proportion of decrease of second frequency data, which is the measurement frequency measured when the user is not specified as being healthy via the operation unit, from the first frequency data associated with the first environmental data having the same order of magnitude as that of second environmental data, which represents the ambient light measured by the imaging unit, to evaluate a degree of fatigue of the user, and displaying the degree of fatigue on the display screen, wherein:

each of the first and second environmental data is a value calculated by $$K \times S_n / S_S,$$

using image luminance data $S_S$ obtained by capturing a reference image at a position having an illuminance of K, and image luminance data $S_n$ obtained by the imaging unit capturing the reference image at a position having an arbitrary illuminance.

A third method for measuring mental fatigue according to the present invention is performed by using a portable terminal device comprising an operation unit, an imaging unit, a display screen, and a recording unit, the method comprising the steps of:

1) measuring ambient light using the imaging unit;
2) displaying a blinking image on the display screen while a flicker frequency of the blinking image is being monotonically changed with time from a start frequency to an ending frequency;
3) recording the flicker frequency in the recording unit, as a measurement frequency, at the time when a user operates the operation unit to indicate that the user perceives flicker during the display of the blinking image;
4) associating first frequency data, which is the measurement frequency measured when the user is specified as being healthy via the operation unit, with first environmental data, which represents the ambient light measured by the imaging unit, and storing the associated data in the recording unit; and
5) calculating a proportion of decrease of second frequency data, which is the measurement frequency measured when the user is not specified as being healthy via the operation unit, from the first frequency data associated with the first environmental data having the same order of magnitude as that of second environmental data, which represents the ambient light measured by the imaging unit, to evaluate a degree of fatigue of the user, and displaying the degree of fatigue on the display screen, wherein:

each of the first and second environmental data is a value calculated by $$\alpha \times K \times H_p / S_S,$$

using image luminance data $S_S$ obtained by capturing a reference image at a position having an illuminance of K, image luminance data $H_p$ obtained by the imaging unit capturing a part of the user's body or an object that the user carries, and a correction factor $\alpha$.

A fourth method for measuring mental fatigue according to the present invention is performed by using a portable terminal device comprising an operation unit, an imaging unit, a display screen, a light-emitting element, and a recording unit, the method comprising the steps of:

1) measuring ambient light using the imaging unit;
2) displaying a blinking image on the light-emitting element while a flicker frequency of the blinking image is being monotonically changed with time from a start frequency to an ending frequency;
3) recording the flicker frequency in the recording unit, as a measurement frequency, at the time when a user operates the operation unit to indicate that the user perceives flicker during the display of the blinking image;
4) associating first frequency data, which is the measurement frequency measured when the user is specified as being healthy via the operation unit, with first environmental data, which represents the ambient light measured by the imaging unit, and storing the associated data in the recording unit; and
5) calculating a proportion of decrease of second frequency data, which is the measurement frequency measured when the user is not specified as being healthy via the operation unit, from the first frequency data associated with the first environmental data having the same order of magnitude as that of second environmental data, which represents the ambient light measured by the imaging unit, to evaluate a degree of fatigue of the user, and displaying the degree of fatigue on the display screen, wherein:

each of the first and second environmental data is a value calculated by $$\alpha \times K \times H_p / S_S,$$

using image luminance data $S_S$ obtained by capturing a reference image at a position having an illuminance of K, image luminance data $H_p$ obtained by the imaging unit capturing a part of the user's body or an object that the user carries, and a correction factor $\alpha$.

A fifth method for measuring mental fatigue according to the present invention is performed in accordance with the above-described third or fourth method for measuring mental fatigue, wherein:

the part of the user's body captured is a palm of a hand; and the correction factor $\alpha$ is a value calculated by $$S_n / H_n,$$

using the image luminance data $S_n$ obtained by capturing the reference image, and image luminance data $H_n$ obtained by capturing the palm of a hand in the same light environment as the data $S_n$.

Advantageous Effects of Invention

The present invention enables easy measurement of human fatigue using a basic function of a portable terminal device, such as a cell phone or PHS, without requiring other external devices.

Further, according to the present invention, the measurement can be performed in an open environment where the user simply observes the blinking image or the blinking light of the light-emitting unit with an about 50 cm interval between the eyes and the portable terminal device; and the user is not forced to look into the measurement device or press his/her eyes onto the measurement device. Therefore, the burden of the user is greatly reduced.

In this method, measurement of ambient light is also carried out at each measurement of human fatigue so as to carry out an evaluation of the degree of fatigue with reference to the data of the user in a generally healthy condition measured under the same ambient light. Therefore, the present invention performs measurements with higher accuracy than the conventional method.

When the data measured at the same ambient light is not found in the history of flicker frequency data, the method calculates a standard flicker frequency for the user in a general healthy condition using plural values from the stored history of flicker frequency data. Therefore, it is possible to accurately evaluate the degree of fatigue even with a relatively small number of measurements.

Further, the method allows for accumulation of data of continuous measurements of the degree of fatigue for a certain period of time, thereby allowing an individual to maintain high-level health management. More specifically, rapidness/moderateness of the change in the degree of fatigue are an important index to determine human health. Therefore, the presentation of information depending on the change in degree of fatigue is useful for health management. For example, if the change in degree of fatigue is more rapid than a certain degree, it is effective to display a message on a cell phone screen such that an immediate care is required; or if the degree of fatigue shows continued periodic extreme amplitude, it is effective to display a message to inform that the user needs some rest and relaxation to ease the amplitude.

Currently, a majority of the population has a cell phone for personal use. The present invention allows for the measurement of fatigue by simply installing a program that performs the method of the present invention onto a cell phone. Chronic fatigue is generally very difficult to notice as a subjective symptom. However, because the program allows a very easy evaluation based on the physiological and objective cognitive reaction of the test subject, the program can improve healthcare management at the individual level, which can further contribute to a decrease in the rate of illnesses, a decrease in the economic burden of medical costs, and improvement in the quality of life.

DESCRIPTION OF EMBODIMENTS

An embodiment of the present invention is described below in reference to the attached drawings. Hereinafter, "fatigue" means mental fatigue, unless otherwise specified.

First Embodiment

Figure 1:
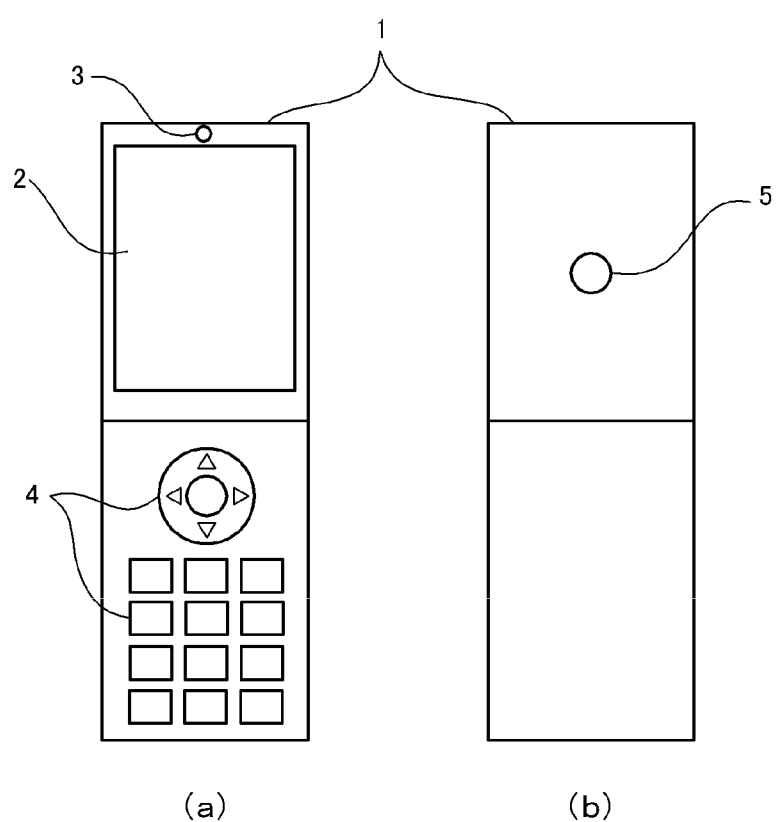
FIG. 1 An external view of a portable terminal device that has a function of measuring mental fatigue, according to an embodiment of the present invention.

FIG. 1 is an exterior view of a portable terminal device, which is a cell phone in this case, having a function of measuring mental fatigue, according to an embodiment of the present invention. FIG. 1(a) is a front view, and FIG. 1(b) is a back view. The cell phone 1 is a general cell phone comprising a liquid crystal screen 2, an LED 3, an operating means 4 such as keys or pads, and a camera lens 5. FIG. 1 illustrates componental members involved in the following operation, omitting the other componental members.

Figure 2:
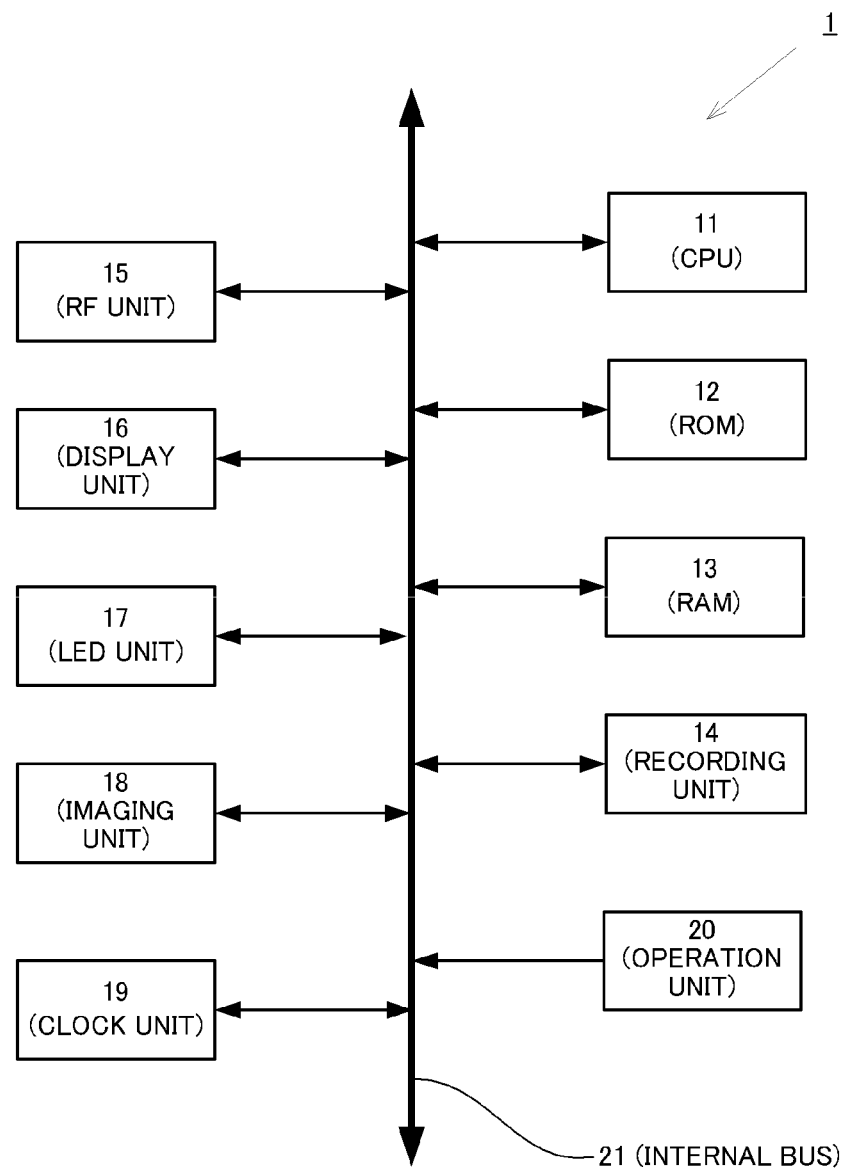
FIG. 2 A block diagram of an internal structure of the portable terminal device shown in FIG. 1.

FIG. 2 is a block diagram showing an internal structure of the cell phone 1. The cell phone 1 includes an arithmetic processing unit (CPU, hereinafter) 11 for controlling the entire operation of the cell phone, a nonvolatile read-only memory (ROM, hereinafter) 12 storing a program etc., a volatile rewritable memory (RAM, hereinafter) 13 for temporarily storing data, a nonvolatile rewritable recording unit 14 for continuously storing data, a communication unit 15 for sending/receiving radio waves to/from a cell phone base station (not shown), a display unit 16, an LED unit 17, an imaging unit 18, a clock unit 19, an operation unit 20, and an internal bus 21 for exchanging data (including control information) between the units. The operation unit 20 includes an operating means 4 such as keys or pads. The display unit 16 includes a liquid crystal screen 2 and a driving unit (not shown) for driving the liquid crystal screen 2. The LED unit 17 includes an LED 3 and a driving unit (not shown) for driving the LED 3. The imaging unit 18 includes an imaging element (not shown) such as a CCD or CMOS sensor, an optical system including a lens 5, and a driving unit (not shown) for driving the lens 5. The clock unit 19 is a means for outputting information of the current time using an internal clock such as a timer.

The cell phone 1 having a function of measuring mental fatigue according to an embodiment of the present invention presents image or light which periodically changes in luminance, using the liquid crystal screen 2 or the LED 3 shown in FIG. 1 and FIG. 2. When the user perceives a blinking in the flashing image or light, the user operates the operating means 4, so that the degree of fatigue of the user is measured and evaluated.

Figure 3:
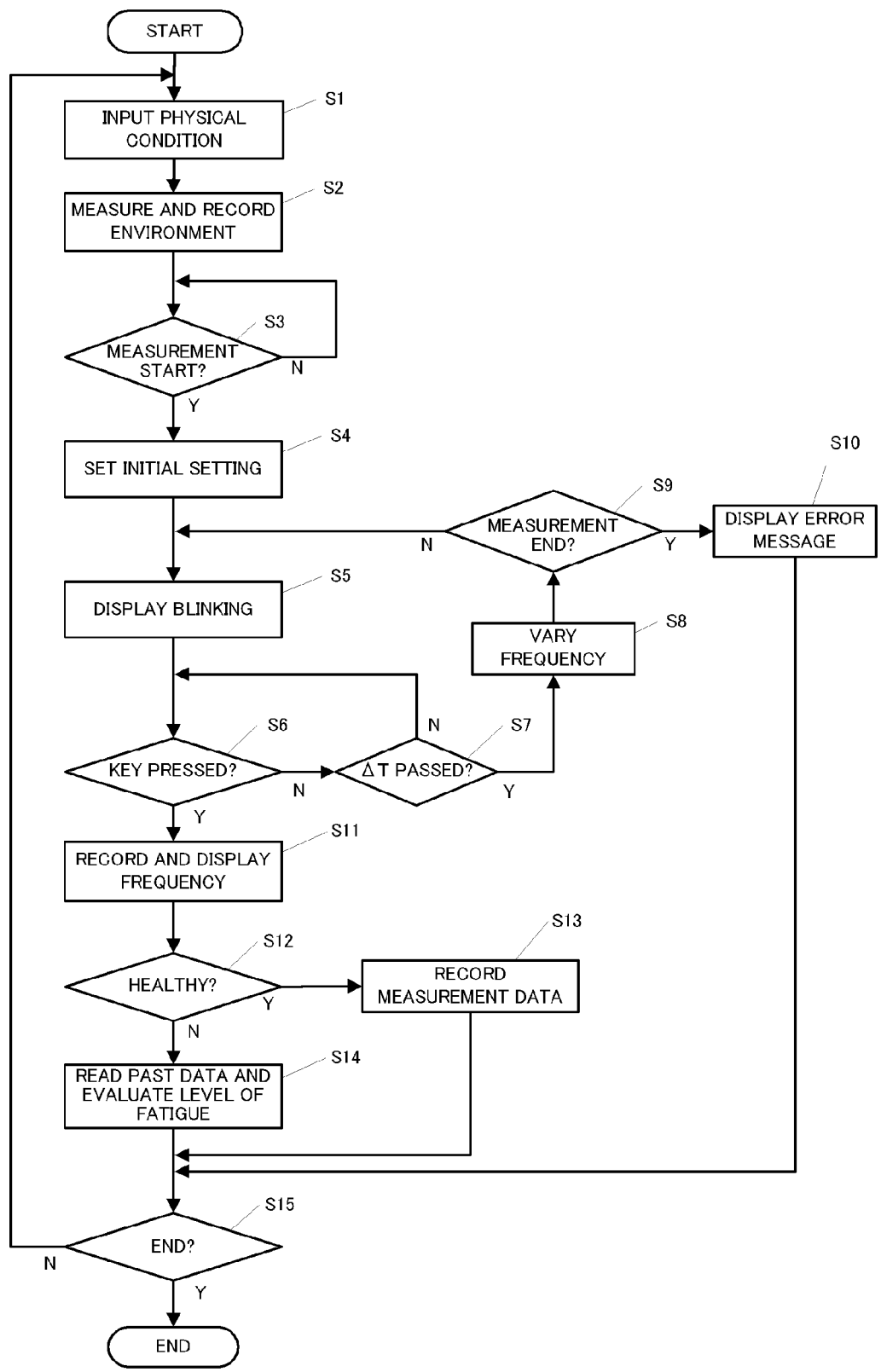
FIG. 3 A flowchart showing operation of the portable terminal device, according to the embodiment of the present invention.

The following describes the details of the measurement and evaluation of mental fatigue according to the present embodiment. FIG. 3 is a flow chart showing operation of the cell phone 1 of the present embodiment. In the following description, all operations are explained as being carried out by the CPU 11, unless otherwise specified. The ROM 12 stores a computer program for allowing the CPU 11 to perform operations described later. The CPU 11 reads out necessary data as required from the ROM 12 and the recording unit 14, processes the data using a predetermined area of the RAM 13 as work area, and stores the temporary results and the final processing results in the recording unit 14 if necessary.

Figure 4:
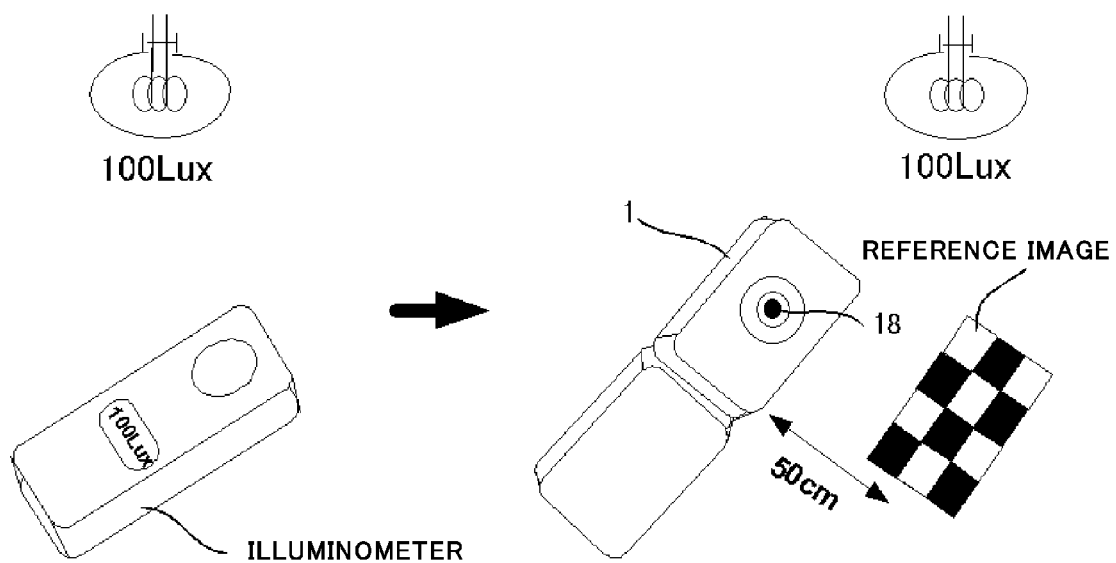
FIG. 4 A schematic view showing how a reference image is captured using a portable terminal device.

It is also assumed that the initial condition required for the measurement is previously stored in the recording unit 14. More specifically, the recording unit 14 of the cell phone 1 previously stores image luminance data obtained by capturing a reference image, and illuminance at the time associated with the image luminance data. FIG. 4 shows an example of image capturing. First, a service provider, who provides a program for evaluating the degree of fatigue, measures illuminance at some points in a luminous environment using an illuminometer to determine a position and direction (the direction of the measurement surface of the illuminometer) in which the illuminance is 100 lux. Next, in the same environment, a cell phone of the same model as the cell phone 1 is used to capture a reference image (e.g., a check pattern printed on a flat surface) arranged in the position and direction in which the illuminance is 100 lux. In FIG. 4, the reference image is captured at a distance of 50 cm from the reference image. To obtain image luminance data, the imaging unit 20 is driven to carry out image-capturing without using a flash under predetermined shooting conditions (including shutter time, focus, distance from the reference image, etc.). This allows the CPU 11 to acquire a signal corresponding to the light quantity received from each pixel of the imaging element. The obtained light quantities are evened off to find an average light quantity per pixel, which is regarded as image luminance data. Insofar as information regarding ambient light is obtained as the image luminance data and a representative data is found from the measured values, statistics other than the average value, such as summation, median, mode, etc., may also be used. The value "100", which indicates the reference illuminance of the measurement, and the image luminance data $S_S$ are stored in a portable recording medium (e.g., a memory card). The recording medium is then provided to the user, who is the owner of the cell phone 1. The illuminance of 100 lux and the image luminance data $S_S$ are stored in the recording unit 14. Here, the image luminance data $S_S$ obtained by a single measurement may be used, or an average of values obtained by multiple measurements may also be used.

First, the liquid crystal screen 2 displays a menu that demands the user to decide whether or not to carry out fatigue measurement. When the user operates the operating means 4 to carry out fatigue measurement, the following fatigue measurement is started.

In Step S1, the user is asked to provide information about the current body condition. For example, the liquid crystal screen 2 displays a question as to whether the user has a healthy body condition or not, and the operation is suspended until the user provides the information. In response to the user's input through the operating means 4, the CPU 11 acquires data corresponding to the user's input of the current body condition, and associates the data with the current time (including day, month, and year) obtained from the clock unit 19 before storing the data in the RAM 13.

In Step S2, ambient light is measured by capturing the reference image, and the measurement result is stored in the RAM 13. More specifically, the imaging unit 18 is driven to carry out image-capturing without using a flash under the same conditions (including shutter time, focus, distance from the reference image, etc.) as when the image luminance data $S_S$ described above is obtained. Thereby, image luminance data ($S_n$) can be obtained, similarly as described above. Then, the illuminance of 100 lux and the image luminance data $S_S$ previously stored in the recording unit are read out, and data N indicating the luminance of the environment (environmental data, hereafter) is obtained by Formula 1. The environmental data corresponds to illuminance.

$$N=100 \times S_n/S_S \qquad \text{(Formula 1)}$$

Here, shooting conditions may be displayed on the display unit 16 so that the user can set the conditions in the cell phone 1, or the CPU 11 may automatically set the shooting conditions.

In Step S3, the sequence is suspended until the measurement start command is inputted. In response to the measurement start command, the sequence goes to Step S4.

In Step S4, the initial condition for the measurement is set. More specifically, a start frequency fs, an end frequency fe, a frequency difference Δf, and a time difference ΔT are read out from the recording unit 14. The start frequency fs is set to a blinking frequency f. For example, the condition is set so that fs=60(Hz), fe=30(Hz), Δf=1.0 (Hz), and ΔT=1 (seconds). Further, the current time is acquired from the clock unit 19 and set to a time parameter T, so as to change the blinking frequency f by the frequency difference Δf using the time difference ΔT (described later).

The following describes operation where fs>fe. As described later, this condition corresponds to a change of the blinking frequency f from a high value to a low value; more specifically, a change from a state where the user cannot perceive the flashing light source as a flicker to a state where the user can perceive the flicker after a certain time has elapsed.

In Step S5, a flashing image or light is presented at the current frequency f=fs determined in Step S4. Incidentally, before or after the flashing presentation, an instruction screen regarding operations with the operating means 4 may be presented to the user. The flashing presentation can be performed using the liquid crystal screen 2 or the LED 3.

Figure 5:
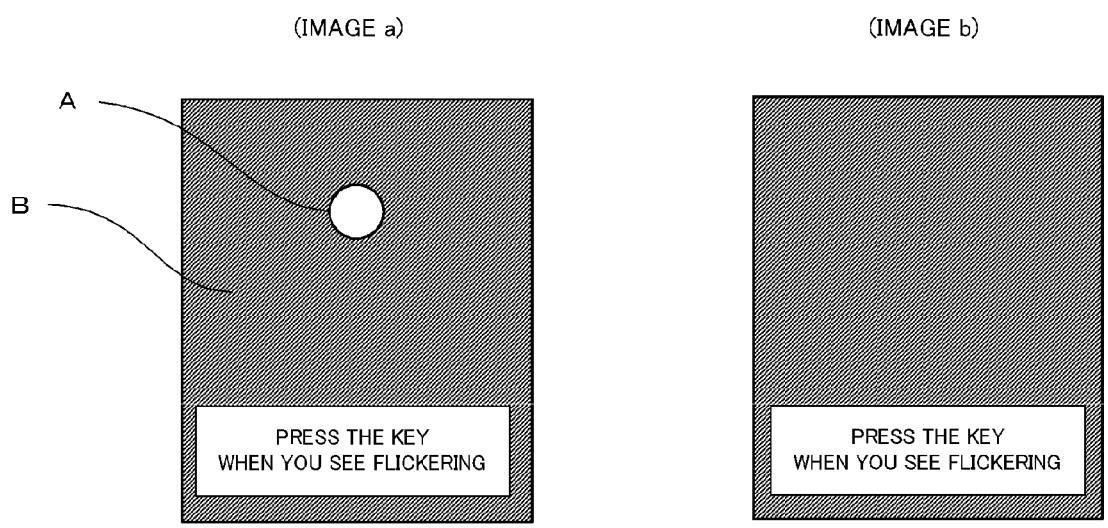
FIG. 5 A view of an example of image data to be displayed in a blinking manner on a liquid crystal screen.

For example, in the case of using the liquid crystal screen 2, a plurality of still images functioning as the flashing light source are previously stored in the recording unit 20. FIG. 5 illustrates an example of two images used as a flashing light source. An image a has the same size (pixels) as that of the liquid crystal screen 2. In the image a, a small region A of a predetermined size having a high luminance is provided in the vicinity of the center, surrounded by a periphery B having a low, uniform luminance. An image b has the same size (pixels) as that of the liquid crystal screen, and has a low, uniform luminance as with the periphery B of the image a. For example, the luminance of the region A is a maximum luminance displayable in the cell phone 1, and the luminance of the periphery B is a minimum luminance displayable in the cell phone 1. More specifically, the region A is a circular region with 100 cd (Candela)/m² in luminance, and about 5 mm in diameter (corresponding to a viewing angle of 0.5 to 0.6° when the cell phone 1 is about 50 cm distant).

The CPU 11 reads out the image a and the image b shown in FIG. 5 into the RAM 13, and alternately transmits these two images to the display unit 16 at predetermined time intervals. The driving unit of the display unit 16 displays the transmitted image data on the liquid crystal screen 2. Here, the CPU 11 calculates the time Δt for displaying each image from the blinking frequency f according to Δt=1/(2×f), repeatedly acquires the current time information from the clock unit 19, and alternately carries out the operation of maintaining the display of either the image a or b until Δt has elapsed, and the operation of switching the display to the other image after the Δt has elapsed. With this sequence of operations, the flashing image of the circle A is displayed to the user at the blinking frequency f. Nevertheless, a text message that reads "please press the key when the image starts flickering" in the image a or b is not flashing and is shown still in the same position.

In the case of using the LED 3, the CPU 11 transmits the blinking frequency f to the driving unit of the LED unit 17 at a predetermined timing. In response to this, the driving unit applies a predetermined voltage which changes at the blinking frequency f to the LED 3, thereby flashing the LED 3. Examples of the voltage to be applied to the LED 3 include a sine wave (cosine wave) and a rectangular wave having a duty ratio of 50%. In this case, for example, a text message that reads "please press the key when the light starts flickering", may be displayed on the liquid crystal screen 2 before the LED starts flashing or during the flashing.

The threshold is determined by either using the frequency at which the user perceives the flicker in the phase of transition from a high speed flashing to a low speed flashing, or a frequency at which the flicker becomes invisible in the phase of reverse transition (low speed flashing to high speed flashing). However, because the frequency at which the user starts perceiving the flicker is a lower value and relatively stable, the present method adopts a frequency at which the user starts perceiving the flicker.

It is desirable to keep the same measuring condition as much as possible, except for that of ambient light. For example, the liquid crystal screen 2 may display a message to instruct the user to look at the flashing image or LED from the front at a distance of about 50 cm from the eyes by simply stretching out his/her arm.

In Step S6, a judgment is carried out as to whether the operating means 4 (keys or the like) have been operated by the user. In Step S5, the liquid crystal screen displays a message "please press a key when the light starts flickering" or the like. If the user presses a key as the user perceives the flicker of the circle A displayed on the liquid crystal screen or the flicker of the LED, the sequence goes to Step S11. If the key is not pressed yet, the sequence goes to Step S7.

In Step S7, the current time t is acquired from the clock unit 19 to be compared with the time parameter T. If the difference (t−T) is smaller than the time difference $\Delta T$ (t−T<$\Delta T$), the sequence goes back to Step S6. If the difference (t−T) is greater than or equal to the time difference $\Delta T$ (t−T≥$\Delta T$), the sequence goes to Step S8.

In Step S8, the frequency difference $\Delta f$ is subtracted from the current blinking frequency f to determine a new blinking frequency f (f=f−$\Delta f$). After the current time t obtained in Step S7 is set to the time parameter T, the sequence goes to Step S9.

In Step S9, a judgment is carried out to determine whether the blinking frequency f exceeds an ending frequency fe. If the judgment concludes as f≥fe, the sequence goes back to Step S5 so that the blinking is given at a new blinking frequency f. If the judgment concludes as f<fe, the sequence goes to Step S10 to carry out an error display, and then goes to Step S15. When the key is not pressed by the user while the blinking is on, the sequence goes to Step S10.

In Step S11, the blinking (or flashing) presentation is stopped, and the value of the current blinking frequency f is displayed on the screen, the current time (including date, month, and year) is acquired from the clock unit 19, and the current time and the blinking frequency f are associated with each other and are stored in the RAM 13.

In Steps S5 to S9, the blinking presentation is carried out while adjusting the blinking frequency f according to the frequency difference $\Delta f$. The adjustment is performed every time the time $\Delta T$, from the start frequency fs to the ending frequency fe, is elapsed. Accordingly, it is possible to obtain a blinking frequency upon the key pressing operation by the user.

In Step S12, the sequence is divided into two operations depending on the data of the body condition stored in the RAM 13 in Step S1. More specifically, if the user has selected that he has a healthy condition in Step S1, the sequence moves to Step S13, and the environmental data N found in Step S2 is associated with the blinking frequency f and the current time stored in the RAM 13 in Step S11. The associated data is stored in the recording unit 14. If the user has not selected that he has a healthy condition in Step S1, the sequence goes to Step S14.

In Step S14, a search is carried out to find a blinking frequency corresponding to the environmental data of a similar degree from the history of measurement results stored in the recording unit 14. Using the blinking frequency as a reference value, the proportion of decrease of the current frequency from the reference value is calculated to evaluate the degree of fatigue of the user, and the evaluation result is displayed on the liquid crystal screen 2. For this operation, it is necessary that the recording unit 14 stores a certain number of history data. If there is no data in the recording unit 14, or the amount is less than required, the liquid crystal screen 2 displays a message that the measurement (evaluation) is not possible.

The "ambient light data of a similar degree" denotes environmental data of the same order of magnitude (having the same most significant digit). The frequency of the threshold at which the flicker is perceived is considered to logarithmically change with respect to the ambient light (luminance). For example, if the ambient luminance is changed from 100 $cd/m^2$ to 10 $cd/m^2$, the frequency of the threshold is assumed to decrease by 1 to 2 Hz. Further, if the luminance of the light-emitting unit is 1000 $cd/m^2$, and the ambient light is less than 1000 $cd/m^2$, the threshold (Hz) decreases by a value of 1.5 times of the logarithmic value of the decrease in luminance. If the ambient light is more than 1000 $cd/m^2$, the threshold (Hz) decreases by a value of three times of the logarithmic value of the decrease in luminance.

Since the threshold frequency measured when the user is in a healthy condition varies depending on the individual difference and age, the evaluation of the degree of fatigue of the user is performed based on the proportion of the decrease from the reference value (percentage on the reference value). For example, a proportion of decrease of 3 to 5% from the reference value is evaluated as "moderate", a proportion of decrease of 5 to 7.5% from the reference value is evaluated as "intermediate", a proportion of decrease of 7.5 to 10% from the reference value is evaluated as "severe", and a proportion of decrease of 10% or greater is evaluated as "hazardous".

When the environmental data close to the current measurement data is not found even though a certain amount of data history is stored in the recording unit 14, interpolation or extrapolation is carried out using plural items of environmental data stored in the recording unit 14 to calculate a frequency corresponding to the currently measured environmental data. The resulting frequency is used as a reference value for the evaluation of degree of fatigue. Accordingly, the evaluation requires history data in an amount sufficient for carrying out the interpolation or extrapolation of the data to enable calculation of the environmental data.

When the environmental data close to the environmental data (B0) measured in Step S2 is not found in the recording unit 14, an alternative calculation is carried out to determine the closest environmental data (B1) in the recording unit 14 with an assumption that an increase of luminance by an order of magnitude increases the threshold by 1.5 Hz (conversely, a decrease of luminance by an order of magnitude decreases the threshold by 1.5 Hz). The blinking frequency (f1) corresponding to the environmental data thus found is read out from the recording unit 14 and is added to a value determined by multiplying the logarithmic value (log(B1−B0)) of the environmental data difference (B1−B0) by 1.5 (Hz), thereby taking the calculated value (f1+1.5×log(B1−B0)) as the reference value.

However, the present invention is not limited to this method, and a newly measured flicker value (f2) may be corrected depending on the light environment. For example, when the environmental data close to the environmental data (B0) measured in Step S2 is not found in the recording unit 14, an alternative calculation is carried out to determine the closest environmental data (B1) in the recording unit 14 with the same assumption as above. The newly measured flicker value f2 is corrected according to f2'=f2+1.5×log(B1−B0). The corrected flicker value f2' is compared with the blinking frequency f1 corresponding to the environmental data B1 (a flicker value of the user in a healthy condition used as a reference value for the evaluation) read out from the recording unit 14 to evaluate the degree of fatigue of the user.

The increased threshold along with an increase of luminance by an order of magnitude (i.e., the decreased threshold value along with a decrease of luminance by an order of magnitude) is not limited to 1.5 Hz. An appropriate value may be used depending on the ambient light and the luminance of the light-emitting unit. For example, it is sometimes preferable to calculate a reference value using 3 Hz in place of 1.5 Hz.

When the amount of data in healthy condition used for the evaluation is less than required, a default value may be used. Though it depends on the device and the experimenter, there are many reports of measurements using a threshold frequency of 42 Hz. When the evaluation is carried out using this value as a reference value, the degree of fatigue based on a change in threshold frequency is determined as follows. A decrease of 1.5 Hz to 2 Hz from the reference value is evaluated as "moderate", a decrease of 2 Hz to 3 Hz from the reference value is evaluated as "intermediate", a decrease of 3 Hz to 4 Hz from the reference value is evaluated as "severe", and a decrease of 4 Hz or greater is evaluated as "hazardous".

Finally, in Step S15, a judgment is carried out to determine whether the instruction of termination is given. If the instruction is not given, the sequence goes back to Step S1. The above described operations are repeated until the instruction of termination is given.

With the above series of operations, the user can easily measure his/her degree of fatigue at any time and in any place.

The present invention is not limited to the description of the embodiment above, and may be altered by making various modifications.

Figure 6:
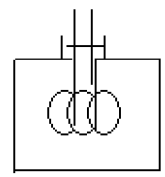
FIG. 6 A schematic view showing how an image of the hand is captured using a portable terminal device.
Figure 6:
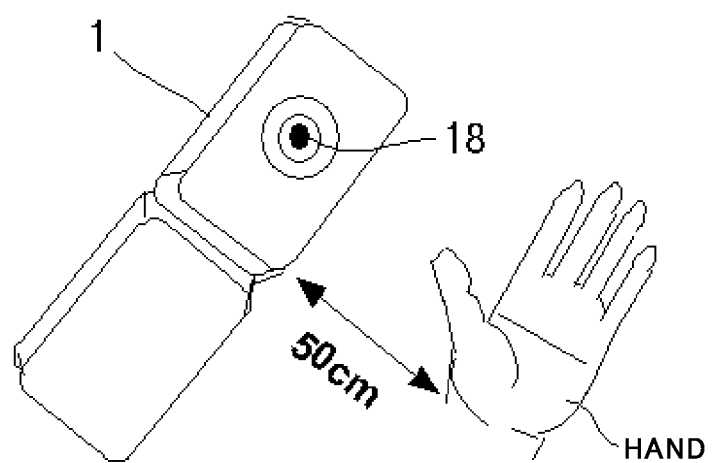

For example, although the user captures a reference image in the above embodiment, the present invention is not limited to this. In the above embodiment, the user is always required to carry the reference image to evaluate the degree of fatigue; however, an image of a part of the user's body or an object that the user usually carries (a wallet, a credit card, a lighter, etc.) can be captured. FIG. 6 shows an example of capturing an image of the user's palm. An image of a standard pattern is captured to obtain image luminance data $S_n$. In the same luminous environment, an image of the palm of a hand arranged in the same position and direction as the standard pattern is captured to obtain image luminance data $H_n$. Here, since the measurements are carried out in the same luminous environment, environmental data to be determined from the image luminance data $H_n$ should be the same value as the environmental data N determined by Formula 1. Accordingly, a correction factor $\alpha$ is introduced, as shown in Formula 2:

$$N = 100 \times S_n/S_S = \alpha \times 100 \times H_n/S_S \quad \text{(Formula 2)}$$

That is, the correction factor $\alpha$ is determined by Formula 3:

$$\alpha = S_n/H_n \quad \text{(Formula 3)}$$

When the correction factor $\alpha$ is previously calculated at least once, and stored, for example, in the cell phone, the user thereafter can obtain environmental data by capturing an image of his/her palm. More specifically, when the user obtains image luminance data $H_p$ by capturing an image of his/her palm in any environment, as shown in FIG. 6, environmental data P can be determined by Formula 4:

$$P = \alpha \times 100 \times H_p/S_S = S_n/H_n \times 100 \times H_p/S_S \quad \text{(Formula 4)}$$

Consequently, the user does not have to carry the reference image. The correction factor $\alpha$ is preferably obtained by averaging values measured several times.

It is preferable to capture images of the same palm (for example, to always capture images of the left palm), and images of either right or left palm can be captured.

The reference illuminance is not limited to 100 lux, and any illuminance level can be used. When the reference illuminance is K lux, the numerical value "100" may be replaced by K in the Formulae 1, 2, and 4.

Though the above embodiment is structured to measure brightness at a reference illuminance for every model of cell phone, and to use the measurement results in the same model of cell phone, the present invention is not limited to this. More specifically, brightness may be measured at a reference illuminance for every manufacturer of cell phones, and the measurement results may be used in cell phones of the same manufacturer. In this case, since cell phones produced by the same manufacturer have different specifications, i.e., an image-capturing system (camera specifications) and display system (number of pixels), depending on the model, it is preferable to carry out measurements using several models of cell phone, and to use the central value (average value, median, mode, etc.) of the measured values.

Moreover, though the above embodiment is structured so that the user determines the correction factor $\alpha$ using data measured by the cell phone 1 (that is, a correction factor is determined for every user), the present invention is not limited to this. For example, the service provider may previously determine correction factors for multiple persons by performing the above measurement, and the central value may be provided to the user's cell phone as a correction factor independent of the user. In this case, the accuracy of evaluating the degree of fatigue might be slightly reduced; however, the user does not have to bother performing a measurement using the reference image.

The reference image is not limited to a monochrome check pattern, as shown in FIG. 4, and may be colored and have any pattern. An image of a uniform luminance with no pattern can also be used. Any object can be used as long as it can be focused on, at least during image capturing. Though it is not easy for the autofocus function of an ordinary cell phone to focus on a uniformly luminous image, it is possible to focus on the target image while the edge of the image is contained in the field of view for imaging.

Although a flicker measurement (e.g., Steps S4 to S11) must be carried out by the user using the cell phone 1, other operations (calculation of environmental data and correction factor, evaluation of fatigue degree, etc.) may be performed by either the cell phone 1 or a server computer (server, hereafter) of the service provider.

For example, the image luminance data $S_S$ measured by the service provider at an illuminance of 100 lux is stored in the server, instead of being provided to the user. When the user transmits the image illuminance data $S_n$ measured by the cell phone 1 to the server, the server calculates environmental data N by Formula 1, and transmits the obtained data N to the user's cell phone 1.

When an image of the hand is captured, the user may transmit the image luminance data $S_n$, the image luminance data $H_n$, and the image luminance data $H_p$ measured by the cell phone 1 to the server from the cell phone 1. The server calculates environmental data P by Formulae 3 and 4, and transmits the obtained environmental data P to the cell phone 1.

Further, when an image of the hand is captured, the user may transmit the image luminance data $S_n$ and the image luminance data $H_n$ measured by the cell phone 1 to the server from the cell phone 1. The server calculates a correction factor $\alpha$ using Formula 3, and transmits the obtained correction factor α to the cell phone 1. In this case, the cell phone 1 calculates the environmental data P using the correction factor α and Formula 4.

Though the above embodiment uses a correction factor determined for each user, correction factors may be previously determined for multiple users, and the central values may be used as a correction factor independent of the user.

For example, in a standard light environment (for example, a light environment often used by the user), a normal flicker value measured in a fatigue-free and healthy condition is uploaded to the server. When the user measures a flicker value in a certain circumstance, the user downloads the normal flicker value stored in the server to the cell phone. The normal value is compared with the measured flicker value to evaluate fatigue based on the decrease of the measured flicker value from the normal value. If there are differences between the measured light environments, correction is made by a correction factor, and evaluation is performed. Normal flicker values may be measured not only in the standard light environment, but also in various light environments, and in a fatigue-free and healthy condition, and the measured values may be uploaded to the server. In this case, the closest normal value(s) in the measured light environment stored in the server is(are) downloaded, and the normal value(s) is(are) compared with the measured flicker value to evaluate fatigue based on the decrease of the measured flicker value. Correction may also be made using a correction factor.

The present invention may be altered by making various modifications to the flow chart in FIG. 3. For example, in the above description of Step S5 to S10, the blinking frequency is linearly decreased; however, the present invention is not limited to this method. For example, the blinking frequency may be increased from a low frequency. Further, insofar as the change is monotonic, the frequency may be increased/decreased nonlinearly. When the blinking frequency is monotonically increased, the start frequency is set smaller than the ending frequency (fs<fe), and the start frequency is set to a value at which the user perceives the flicker. The liquid crystal screen may display an instruction such as operating a key when the flicker becomes unperceivable.

Instead of using only one kind of initial condition, i.e., one kind of the set of start frequency fs, ending frequency fe, frequency difference Δf, and time difference ΔT, it is possible to previously store plural different initial conditions in the recording unit 14, and reads out one of them at random in Step S4 of setting the initial condition. With this variation, the user cannot predict the timing of the perception of the flicker from the beginning of the measurement even when the user performs the test frequently. As a result, the accuracy of the measurement result increases. By varying at least one value among the four parameters (fs, fe, Δf, ΔT) of the initial conditions, the prediction of the timing becomes difficult. For example, under the condition where fs=60 (Hz), fe=30 (Hz), and ΔT=1 (seconds), the Δf can be varied among 1.2, 1.0 and 0.8 Hz.

The threshold may also be determined by repeating Steps S4 to S13 for 3 to 5 times, selecting measurements with a difference of 1 Hz or less, and finding an average of the measurements.

The device used for the measurement is not limited to cell phones. Examples of the devices include portable terminal devices having an imaging means, such as a PHS (Personal Handyphone System) and a PDA (Personal Digital Assistant). Further, the display screen is not limited to liquid crystal screens. For example, a cell phone having a kind of display screen other than liquid crystal, such as an EL display (Electroluminescence Display) may be used. Further, instead of a cell phone containing an LED, it is possible to use a light-emitting element capable of emitting visible light and flashing the light at a predetermined frequency.

Further, though the above embodiment uses two images as the images displayed on the liquid crystal screen, the present invention is not limited to this structure, and three or more images may be used. For example, an image c, which has an intermediate luminance of the images a and b in FIG. 5, may be used so that the screen repeatedly displays images in the order of image a→image c→image b→image a. For example, the image c is created by finding an average of the corresponding pixel data of the image a and the image b. In this case, in Step S5, the time for displaying each image Δt is determined using the blinking frequency f according to Δt=1/(3×f). When a plurality of images is used, the time for displaying each image is appropriately set depending on the luminance of the image being used. Moreover, instead of using an image in which a part of the pixels of the image has a different luminance from those of the rest of the pixels, it is also possible to use plural images that each have a different uniform luminance.

Further, instead of preparing images to be displayed in advance, it is possible to cause the CPU 11 to generate images and store them in the RAM 13 before the measurement, and carry out the blinking display using the images.

Though the above embodiment is structured so that the program for measuring the degree of mental fatigue is previously stored in the ROM 12, it is also possible to download the program to the cell phone by accessing an Internet server, or installing the program in the cell phone via a detachable recording medium, such as a memory card.

Though the above embodiment is structured so that the recording unit stores only the result of the measurement in which the user determines that the user is in healthy condition, it is also possible to store the result of the measurement in which the user determines that the user is not in healthy condition. In this case, the perceived blinking frequency, the current time (including day, month, and year), the ambient environmental data, and the evaluation results of the degree of fatigue are associated with each other in the recording unit. Further, it is possible to transmit data from the recording unit 14 to a computer server or the like at certain time intervals or in response to the user's instruction, thereby storing data for a long period as a database. Storage to the database may be performed via a detachable recording medium, such as a memory card. As such, the degree of fatigue can be continuously measured and evaluated at a certain period of time, and the measurement and the evaluation data can be accumulated. This enables high-level of health management for individuals.

It is also possible to determine the user's health condition based on a combination of the blinking measurement results accumulated over a certain period of time and other physiological indices. In the case the user uses his/her cell phone to access to the server, the server may carry out an evaluation of the health condition of the user in response to the access, transmitting the evaluation results to the cell phone of the user, having them displayed on the screen of the cell phone.

These are described in detail below.

Second Embodiment

Hereinbelow, a method for storing and managing data obtained by the method described above and a method for determining a biological state are explained.

1) Storage and Management of Measurement Data

Flicker values measured by the user using a portable terminal device, flicker values corrected according to the light environment, and light intensity values of the light environment are transmitted to the server from the portable terminal device, and are recorded by the server. The server transmits a display image of data to the portable terminal device on a several-day, several-week, or several-month basis as the need arises (for example, when the server receives a request from the user's cell phone). Further, the server rearranges data by factors such as the light environment, time, working conditions, subjective conditions of fatigue, and the like, which are recorded as measurement condition information at the same time that the measurement is performed. Then, the server generates a graph or the like, and transmits the generated graph or the like to the portable terminal device.

2) Determination and Notification of Abnormal Values

The server evaluates whether the measure flicker values is an abnormal value. When the server determines that it is an abnormal value, the server transmits specified information to the portable terminal device in order to notify the user of the condition. In regard to the determination of abnormal values, the server determines that the measured flicker value is an abnormal value when data $F_N$ of a newly measured flicker value received by the server deviates by a certain value or more (for example, 10 Hz or more) from an average value of accumulated data (the accumulated data refers to, among flicker values $F_1$ measured when the user was specified as being healthy, the flicker values associated with the ambient light (i.e., environmental data; the same applies hereinafter) that is the same or approximate to that under which a new flicker value $F_N$ was measured); or when data $F_N$ deviates by a certain value or more (for example, 1.5σ or more) from an average value of accumulated data (the same as defined above) based on the dispersion σ of the accumulated data. The server transmits information regarding the determination to the portable terminal device.

The server determines abnormal values by using the information of all the data and further evaluates the measurement data by setting limits by using the measurement condition information. In regard to flicker values, there has been a report on a phenomenon called the "weekend effect" in which flicker values are high in the beginning of the week and become lower towards the weekend due to an accumulation of fatigue. Accordingly, abnormal values are determined by analyzing the measurement data using, for example, only the data from Mondays or Fridays. This allows a more precise understanding of abnormal conditions.

3) Determination and Notification of Abnormal Tendencies

The server compares the measured data and previous data, and catches tendencies for change in the data. When the manner of the change is abnormal or sharp to a certain degree or more, the server determines that the change indicates an abnormal tendency, and sends notice of this determination to the terminal device. Specifically, when the server receives new data (luminance data and flicker value), the server selects, among a plurality of recorded data (i.e., data measured when the user was not specified as being healthy), multiple flicker values associated with the luminance data that is the same or approximate to the newly received luminance data. Then, for example, the server compares an average value of the plurality of selected flicker values and the newly measured flicker values, or evaluates the tendency of a change in multiple data (flicker values) including the newly received flicker values in addition to the selected flicker values. For example, in regard to the above-described weekend effect, when the frequency is reduced from 40 Hz to 35 Hz under a normal condition, it is considered to be a normal weekend effect. However, when the frequency is reduced from 40 Hz to 25 Hz under a given condition, or when the frequency has already reached 35 Hz in the middle of the week, it is considered that an obviously extreme shape change is occurring in the flicker value. Consequently, the server determines that the change indicates an abnormal tendency, and transmits the determination information to the terminal device. Additionally, under normal conditions, the flicker value is likely to gradually decrease from Monday to Friday; however, when the value fluctuates extremely, or when the value shows an increase, it is suspected that there is a problem with the biological state, the measuring conditions, or the like. Accordingly, such a change in the flicker value is regarded as an abnormal tendency, and this information is sent to the terminal device.

4) Submission of Fatigue Process Information and Break Reminder

The server provides fatigue process information. The server determines how many Hz the newly measured flicker value decreased from the value registered as the healthy value (the value when the user is not fatigued) as well as the average of all the previous values and the average of the values within a month or the last 3 times. Further, the server evaluates the fatigue of the user based on what percentage the value decreased from the healthy value. Then, the server transmits and displays the information regarding the level of fatigue to the terminal device. It is known that when the flicker value decreases from the healthy value by about 10%, the result of the Kraepelin test, in which the subject adds single-digit numbers, will be extremely low. It is also known that the labor of driving a vehicle for 24 hours results in a decrease of about 15% in the flicker value. For example, in the case where a rate of decrease in the flicker value relative to the healthy value that is within the range of 0 to 5% is specified as mild fatigue, while a rate within the range of 5 to 10% is specified as moderate fatigue, and a rate within the range of 10 to 15% is specified as severe fatigue, the server determines the level of fatigue based on the measured flicker value, and transmits information corresponding to the determination result to the terminal device. For example, when the user is determined to be experiencing severe fatigue, the server displays a break reminder. The server also displays a break reminder when a decrease in the flicker value from the flicker value on the previous day is greater by a certain degree or more than a decrease that would occur in the normal process. Further, when a decrease in the flicker value is clearly indicated on the weekend, particularly on Friday, as compared to Monday, the server displays on the terminal device that the weekend effect has been observed, as well as a break reminder.

Third Embodiment

Hereinafter, in addition to the flicker values, the use of biological information and physiological index information is explained.

1) When an Acceleration Meter (Hereinafter Sometimes Referred to as an "Acceleration Sensor") is Used The user is required to carry an acceleration sensor (which may be provided separately from the cell phone, or embedded in the cell phone), and a correlation between information obtained by the acceleration sensor and the flicker value is evaluated. Specifically, the acceleration detected by the acceleration sensor at a specific timing is transmitted to the server along with the information on the time of detection, and all of this information is recorded by the server. Under normal conditions, the amount of change in the acceleration (for example, temporal change in the value obtained by time integration of the measured acceleration for a certain period of time) indicates the sum of biological activities. Therefore, a higher value of acceleration is presumed to indicate a larger amount of activity, i.e., more work has been performed, and it is determined that the flicker value decreases accordingly. In this case, the following conditions are presumed: a normal condition in which an increase in the amount of change in the acceleration and a decrease in the flicker value are simultaneously observed (specifically, the fatigue progresses along with an increase in the value of the integrated acceleration from when the user was in a healthy condition, and a decrease in the flicker value is observed along with the progress of fatigue); abnormal condition A in which the amount of change detected by the acceleration sensor increases although not by much, and the decrease in the flicker value is sharp; and abnormal condition B in which although the acceleration sensor detects a very large amount of change, not much of a decrease in the flicker value is observed. After the flicker value is measured, the value is checked against the amount of change detected by the acceleration sensor. When the condition is determined to be abnormal condition A or abnormal condition B, the server displays the result on the terminal device.

2) Use of Other Physiological Index Information

When data such as physiological index information (e.g., heart rate (R-R interval) and blood pressure) and biochemical indices of saliva and blood (e.g., cortisol, cytokine, and essential trace metals (such as zinc)) is measured on-line or off-line along with a flicker value, the values of the above data are compared with the flicker value. The server displays information indicating a normal condition to the terminal device when the values of the above data change in correlation with the flicker value, or information indicating an abnormal condition when these values are extremely high or low.

INDUSTRIAL APPLICABILITY

The portable terminal device having a function of measuring mental fatigue, the measuring method thereof, and the server computer of the present invention enable easy measurement of human fatigue using a standard functions of the portable terminal device, for example, a cell phone or PHS, without requiring other external devices.

REFERENCE NUMERALS

1 Portable terminal device (cell phone)
2 Liquid crystal screen
3 LED
4 Operating means
5 Camera lens
11 Central processing unit (CPU)
12 Read-only memory (ROM)
13 Rewritable memory (RAM)
14 Recording unit
15 Communication unit
16 Display unit
17 LED unit
18 Imaging unit
19 Clock unit
20 Operation unit
21 Internal bus

The invention claimed is:
1. A portable terminal device capable of measuring mental fatigue comprising:

a processor configured to calculate a first frequency data and a second frequency data;
an operation unit;
an imaging unit configured to measure ambient light, the imaging unit comprising a CCD or CMOS sensor and a lens;
a display screen configured to display a blinking image while a flicker frequency of the blinking image is being monotonically changed with time from a start frequency to an ending frequency; and
a memory configured to record the flicker frequency, as a measurement frequency, at the time when a user operates the operation unit to indicate that the user perceives flicker during the display of the blinking image,
wherein:
the first frequency data is associated with first environmental data, which represents the ambient light measured by the imaging unit, the first frequency data being the measurement frequency measured when the user is specified as being healthy via the operation unit, and an associated data of the first frequency data and the first environmental data is stored in the memory; and
a proportion of decrease of the second frequency data from the first frequency data, the first frequency data being associated with the first environmental data, the first environmental data having the same order of magnitude as that of second environmental data, the proportion of decrease of the second frequency is calculated to evaluate a degree of fatigue of the user, the second frequency data being the measurement frequency measured when the user is not specified as being healthy via the operation unit, the second environmental data being the ambient light measured by the imaging unit, and the degree of fatigue is displayed on the display screen,
wherein:
each of the first and second environmental data is a value calculated by first environmental data=$K \times S_n/S_S$, and second environmental data=$K \times S_n/S_S$, using image luminance data $S_S$ obtained by capturing a reference image at a position having a reference illuminance of K; and image luminance data $S_n$ obtained by the imaging unit capturing the reference image at a position having an arbitrary illuminance, and
wherein the processor uses the reference illuminance of K to correct the image luminance data $S_n$.

2. A portable terminal device capable of measuring mental fatigue comprising:
a processor configured to calculate a first frequency data and a second frequency data;
an operation unit;
an imaging unit configured to measure ambient light, the imaging unit comprising a CCD or CMOS sensor and a lens;
a display screen;
a light-emitting element configured to display a blinking image while a flicker frequency of the blinking image is being monotonically changed with time from a start frequency to an ending frequency; and
a memory configured to record the flicker frequency, as a measurement frequency, at the time when a user operates the operation unit to indicate that the user perceives flicker during the display of the blinking image, wherein:

the first frequency data is associated with first environmental data, which represents the ambient light measured by the imaging unit, the first frequency data being the measurement frequency measured when the user is specified as being healthy via the operation unit, and an associated data of the first frequency data and the first environmental data is stored in the memory; and a proportion of decrease of the second frequency data from the first frequency data, the first frequency data being associated with the first environmental data, the first environmental data having the same order of magnitude as that of second environmental data, the proportion of decrease of the second frequency is calculated to evaluate a degree of fatigue of the user, the second frequency data being the measurement frequency measured when the user is not specified as being healthy via the operation unit, the second environmental data being the ambient light measured by the imaging unit, and the degree of fatigue is displayed on the display screen, wherein:

each of the first and second environmental data is a value calculated by first environmental data=$K \times S_n/S_S$, and second environmental data=$K \times S_n/S_S$, using image luminance data $S_S$ obtained by capturing a reference image at a position having a reference illuminance of K; and image luminance data $S_n$ obtained by the imaging unit capturing the reference image at a position having an arbitrary illuminance, and wherein the processor uses the reference illuminance of K to correct the image luminance data $S_n$.

3. A portable terminal device capable of measuring mental fatigue comprising:

a processor configured to calculate a first frequency data and a second frequency data;

an operation unit;

an imaging unit configured to measure ambient light, the imaging unit comprising a CCD or CMOS sensor and a lens;

a display screen configured to display a blinking image while a flicker frequency of the blinking image is being monotonically changed with time from a start frequency to an ending frequency; and a memory configured to record the flicker frequency, as a measurement frequency, at the time when a user operates the operation unit to indicate that the user perceives flicker during the display of the blinking image, wherein:

the first frequency data is associated with first environmental data, which represents the ambient light measured by the imaging unit, the first frequency data being the measurement frequency measured when the user is specified as being healthy via the operation unit, and an associated data of the first frequency data and the first environmental data is stored in the memory; and a proportion of decrease of the second frequency data from the first frequency data, the first frequency data being associated with the first environmental data, the first environmental data having the same order of magnitude as that of second environmental data, the proportion of decrease of the second frequency is calculated to evaluate a degree of fatigue of the user, the second frequency data being the measurement frequency measured when the user is not specified as being healthy via the operation unit, the second environmental data being the ambient light measured by the imaging unit, and the degree of fatigue is displayed on the display screen, wherein:

each of the first and second environmental data is a value calculated by first environmental data=$\alpha \times K \times H_p/S_S$, and second environmental data=$\alpha \times K \times H_p/S_S$, using image luminance data $S_S$ obtained by capturing a reference image at a position having a reference illuminance of K, image luminance data $H_p$ obtained by the imaging unit capturing a part of the user's body or an object that the user carries, and a correction factor α, and wherein the processor uses the reference illuminance of K to correct the image luminance data $H_p$.

4. A portable terminal device capable of measuring mental fatigue comprising:

a processor configured to calculate a first frequency data and a second frequency data;

an operation unit;

an imaging unit configured to measure ambient light, the imaging unit comprising a CCD or CMOS sensor and a lens;

a display screen;

a light-emitting element configured to display a blinking image while a flicker frequency of the blinking image is being monotonically changed with time from a start frequency to an ending frequency; and a memory configured to record the flicker frequency, as a measurement frequency, at the time when a user operates the operation unit to indicate that the user perceives flicker during the display of the blinking image, wherein:

the first frequency data is associated with first environmental data, which represents the ambient light measured by the imaging unit, the first frequency data being the measurement frequency measured when the user is specified as being healthy via the operation unit, and an associated data of the first frequency data and the first environmental data is stored in the memory; and a proportion of decrease of the second frequency data from the first frequency data, the first frequency data being associated with the first environmental data, the first environmental data having the same order of magnitude as that of second environmental data, the proportion of decrease of the second frequency is calculated to evaluate a degree of fatigue of the user, the second frequency data being the measurement frequency measured when the user is not specified as being healthy via the operation unit, the second environmental data being the ambient light measured by the imaging unit, and the degree of fatigue is displayed on the display screen, wherein:

each of the first and second environmental data is a value calculated by first environmental data=$\alpha \times K \times H_p/S_S$, and second environmental data=$\alpha \times K \times H_p/S_S$, using image luminance data $S_S$ obtained by capturing a reference image at a position having a reference illuminance of K, image luminance data $H_p$ obtained by the imaging unit capturing a part of the user's body or an object that the user carries, and a correction factor α, and wherein the processor uses the reference illuminance of K to correct the image luminance data $H_p$.

5. The portable terminal device capable of measuring mental fatigue according to claim 3 or 4,
wherein:
the part of the user's body captured is a palm of a hand, and the correction factor α is a value calculated by $$S_n/H_n,$$

using the image luminance data $S_n$ obtained by capturing the reference image, and image luminance data $H_n$ obtained by capturing the palm of a hand in the same light environment as the data $S_n$.

6. A server computer for determining an abnormal state of the user in accordance with a change in data measured by the portable terminal device of any one of claims 1 to 2,
wherein:
the first frequency data and first environmental data measured by the portable terminal device, and information of a time at which these data are measured are received from the portable terminal device and stored; and
when the second frequency data and second environmental data are received from the portable terminal device, and when the difference between the second frequency data and the first frequency data associated with the first environmental data having the same order of magnitude as that of the second environmental data is equal to or greater than a predetermined value, an abnormal state of the user is determined, and information corresponding to the determination result is transmitted to the portable terminal device.

7. A server computer for determining an abnormal state of the user in accordance with a change in data measured by the portable terminal device of any one of claims 1 to 2,
wherein:
the second frequency data and second environmental data measured by the portable terminal device, and information of a time at which these data are measured are received from the portable terminal device and stored; and
when new second frequency data and new second environmental data are received from the portable terminal device, the second frequency data associated with the second environmental data having the same order of magnitude as that of the new second environmental data is selected, and when a variation with time between the selected second frequency data and the new second environmental data differs from that of a weekend effect, an abnormal state of the user is determined, and information corresponding to the determination result is transmitted to the portable terminal device.

8. A server computer for determining an abnormal state of the user in accordance with a change in data measured by the portable terminal device of any one of claims 1 to 2,
wherein:
the second frequency data and second environmental data measured by the portable terminal device, and information of a time at which these data are measured are received from the portable terminal device and stored; and
acceleration data detected by an acceleration sensor that the user carries, and information of a time at which the acceleration data is detected are received and stored; and
a change in the second frequency data associated with the second environmental data having the same order of magnitude, and a change in the acceleration data, both of which occurred within a predetermined period, are evaluated to determine an abnormal state of the user, and information corresponding to the determination result is transmitted to the portable terminal device.

9. A method for measuring mental fatigue using a portable terminal device comprising a processor, an operation unit, an imaging unit, wherein the imaging unit comprises a CCD or CMOS sensor and a lens, a display screen, and a memory,
the method comprising the steps of:
1) measuring ambient light using the imaging unit with the CCD sensor or CMOS sensor and the lens;
2) displaying a blinking image on the display screen while a flicker frequency of the blinking image is being monotonically changed with time from a start frequency to an ending frequency;
3) recording the flicker frequency in the memory, as a measurement frequency, at the time when a user operates the operation unit to indicate that the user perceives flicker during the display of the blinking image;
4) associating a first frequency data with first environmental data, which represents the ambient light measured by the imaging unit, the first frequency data being the measurement frequency measured when the user is specified as being healthy via the operation unit, and storing an associated data of the first frequency data and the first environmental data in the memory; and
5) calculating a proportion of decrease of a second frequency data by the processor from the first frequency data, the first frequency data being associated with the first environmental data, the first environmental data having the same order of magnitude as that of second environmental data to evaluate a degree of fatigue of the user, the second frequency data being the measurement frequency measured when the user is not specified as being healthy via the operation unit, the second environmental data being the ambient light measured by the imaging unit, and displaying the degree of fatigue on the display screen,
wherein:
each of the first and second environmental data is a value calculated by first environmental data=$K \times S_n/S_S$, and second environmental data=$K \times S_n/S_S$, using image luminance data $S_S$ obtained by capturing a reference image at a position having a reference illuminance of K, and image luminance data $S_n$ obtained by the imaging unit capturing the reference image at a position having an arbitrary illuminance, and
wherein the processor uses the reference illuminance of K to correct the image luminance data $S_n$.

10. A method for measuring mental fatigue using a portable terminal device comprising a processor, an operation unit, an imaging unit, wherein the imaging unit comprises a CCD or CMOS sensor and a lens, a display screen, a light-emitting element, and a memory,
the method comprising the steps of:
1) measuring ambient light using the imaging unit with the CCD sensor or CMOS sensor and the lens;
2) displaying a blinking image on the light-emitting element while a flicker frequency of the blinking image is being monotonically changed with time from a start frequency to an ending frequency;
3) recording the flicker frequency in the memory, as a measurement frequency, at the time when a user operates the operation unit to indicate that the user perceives flicker during the display of the blinking image;
4) associating a first frequency data with first environmental data, which represents the ambient light measured by the imaging unit, the first frequency data being the measurement frequency measured when the user is specified as being healthy via the operation unit, and storing an associated data of the first frequency data and the first environmental data in the memory; and 5) calculating a proportion of decrease of a second frequency data by the processor from the first frequency data, the first frequency data being associated with the first environmental data, the first environmental data having the same order of magnitude as that of second environmental data to evaluate a degree of fatigue of the user, the second frequency data being the measurement frequency measured when the user is not specified as being healthy via the operation unit, the second environmental data being the ambient light measured by the imaging unit, and displaying the degree of fatigue on the display screen, wherein:

each of the first and second environmental data is a value calculated by first environmental data=$K \times S_n/S_S$, and second environmental data=$K \times S_n/S_S$, using image luminance data $S_S$ obtained by capturing a reference image at a position having a reference illuminance of K, and image luminance data $S_n$ obtained by the imaging unit capturing the reference image at a position having an arbitrary illuminance, and wherein the processor uses the reference illuminance of K to correct the image luminance data $S_n$.

11. A method for measuring mental fatigue using a portable terminal device comprising a processor, an operation unit, an imaging unit, wherein the imaging unit comprises a CCD or CMOS sensor and a lens, a display screen, and a memory, the method comprising the steps of:

1) measuring ambient light using the imaging unit with the CCD sensor or CMOS sensor and the lens;
2) displaying a blinking image on the display screen while a flicker frequency of the blinking image is being monotonically changed with time from a start frequency to an ending frequency;
3) recording the flicker frequency in the memory, as a measurement frequency, at the time when a user operates the operation unit to indicate that the user perceives flicker during the display of the blinking image;
4) associating a first frequency data with first environmental data, which represents the ambient light measured by the imaging unit, the first frequency data being the measurement frequency measured when the user is specified as being healthy via the operation unit; and storing an associated data of the first frequency data and the first environmental data in the memory; and
5) calculating a proportion of a decrease of second frequency data by the processor from the first frequency data, the first frequency data being associated with the first environmental data, the first environmental data having the same order of magnitude as that of second environmental data to evaluate a degree of fatigue of the user, the second frequency data being the measurement frequency measured when the user is not specified as being healthy via the operation unit, the second environmental data being the ambient light measured by the imaging unit, and displaying the degree of fatigue on the display screen, wherein:

each of the first and second environmental data is a value calculated by first environmental data=$\alpha \times K \times H_p/S_S$, and second environmental data=$\alpha \times K \times H_p/S_S$, using image luminance data $S_S$ obtained by capturing a reference image at a position having an illuminance of K, image luminance data $H_p$ obtained by the imaging unit capturing a part of the user's body or an object that the user carries, and a correction factor α, and wherein the processor uses the reference illuminance of K to correct the image luminance data $H_p$.

12. A method for measuring mental fatigue using a portable terminal device comprising a processor, an operation unit, an imaging unit, wherein the imaging unit comprises a CCD or CMOS sensor and a lens, a display screen, a light-emitting element, and a memory, the method comprising the steps of:

1) measuring ambient light using the imaging unit with the CCD sensor or CMOS sensor and the lens;
2) displaying a blinking image on the light-emitting element while a flicker frequency of the blinking image is being monotonically changed with time from a start frequency to an ending frequency;
3) recording the flicker frequency in the memory, as a measurement frequency, at the time when a user operates the operation unit to indicate that the user perceives flicker during the display of the blinking image;
4) associating a first frequency data with first environmental data, which represents the ambient light measured by the imaging unit, the first frequency data being the measurement frequency measured when the user is specified as being healthy via the operation unit, and storing an associated data of the first frequency data and the first environmental data in the memory; and
5) calculating a proportion of a decrease of second frequency data by the processor from the first frequency data, the first frequency data being associated with the first environmental data, the first environmental data having the same order of magnitude as that of second environmental data to evaluate a degree of fatigue of the user, the second frequency data being the measurement frequency measured when the user is not specified as being healthy via the operation unit, the second environmental data being the ambient light measured by the imaging unit, and displaying the degree of fatigue on the display screen, wherein:

each of the first and second environmental data is a value calculated by first environmental data=$\alpha \times K \times H_p/S_S$, and second environmental data=$\alpha \times K \times H_p/S_S$, using image luminance data $S_S$ obtained by capturing a reference image at a position having an illuminance of K, image luminance data $H_p$ obtained by the imaging unit capturing a part of the user's body or an object that the user carries, and a correction factor α, and wherein the processor uses the reference illuminance of K to correct the image luminance data $H_p$.

13. The method for measuring mental fatigue according to claim 11 or 12, wherein:

the part of the user's body captured is a palm of a hand; and the correction factor α is a value calculated by $S_n/H_n$, using the image luminance data $S_n$ obtained by capturing the reference image, and image luminance data $H_n$ obtained by capturing the palm of a hand in the same light environment as the data $S_n$.

* * * * *